(12) United States Patent
Seddon et al.

(10) Patent No.: US 9,463,063 B2
(45) Date of Patent: Oct. 11, 2016

(54) ELECTROSURGICAL DEVICE AND SYSTEM

(71) Applicant: Boston Scientific Scimed, Inc., Maple Grove, MN (US)

(72) Inventors: Dane Seddon, Boston, MA (US); Sean Fleury, Brighton, MA (US); Mark Wood, Shrewsbury, MA (US); Peter Dayton, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/689,481

(22) Filed: Apr. 17, 2015

(65) Prior Publication Data

US 2015/0238254 A1    Aug. 27, 2015

Related U.S. Application Data

(63) Continuation of application No. 13/781,222, filed on Feb. 28, 2013, now Pat. No. 9,033,975.

(60) Provisional application No. 61/604,817, filed on Feb. 29, 2012.

(51) Int. Cl.
*A61B 18/18* (2006.01)
*A61B 18/14* (2006.01)
*A61B 17/00* (2006.01)

(52) U.S. Cl.
CPC ........... *A61B 18/1492* (2013.01); *A61B 18/14* (2013.01); *A61B 18/1482* (2013.01); *A61B 2017/003* (2013.01); *A61B 2017/00305* (2013.01); *A61B 2017/00314* (2013.01); *A61B 2017/00323* (2013.01)

(58) Field of Classification Search
None
See application file for complete search history.

(56) References Cited

U.S. PATENT DOCUMENTS

| 3,060,972 A * | 10/1962 | Sheldon ............... A61B 1/0055 |
| | | 138/120 |
| 5,192,280 A | 3/1993 | Parins |
| 5,383,852 A | 1/1995 | Stevens-Wright |
| 5,441,499 A | 8/1995 | Fritzsch |

(Continued)

FOREIGN PATENT DOCUMENTS

| EP | 0900547 A1 | 3/1999 |
| EP | 1857061 A1 | 11/2007 |

(Continued)

OTHER PUBLICATIONS

International Preliminary Report on Patentability for corresponding International Application No. PCT/US2013/028352, issued on Sep. 2, 2014, (7 pages).

*Primary Examiner* — Brian T Gedeon
(74) *Attorney, Agent, or Firm* — Bookoff McAndrews, PLLC

(57) ABSTRACT

Embodiments of the disclosure include devices and systems for using an end effector. In an embodiment, a medical device may include an articulation section. The articulation section may be operatively associated with an elongate articulation member configured to move the articulation section, wherein the articulation section can be configured to receive part of a conductive member. The medical device may also include an end effector. The end effector may include an electrode and a non-conductive section encasing a junction between the electrode and the conductive member, wherein the non-conductive section can be moveably coupled to the articulation section and can be fixedly coupled to the elongate articulation member.

18 Claims, 7 Drawing Sheets

(56) References Cited

U.S. PATENT DOCUMENTS

| | | | |
|---|---|---|---|
| 5,454,827 A | 10/1995 | Aust et al. | |
| 5,540,706 A | 7/1996 | Aust et al. | |
| 5,749,828 A * | 5/1998 | Solomon | A61B 1/0055 600/139 |
| 6,030,360 A | 2/2000 | Biggs | |
| 6,663,641 B1 | 12/2003 | Kovac et al. | |
| 6,743,239 B1 | 6/2004 | Kuehn et al. | |
| 7,637,905 B2 * | 12/2009 | Saadat | A61B 1/0055 600/104 |
| 7,682,307 B2 * | 3/2010 | Danitz | A61B 1/0055 600/141 |
| 7,837,620 B2 * | 11/2010 | Nobis | A61B 1/00071 600/139 |
| 8,083,667 B2 * | 12/2011 | Cooper | A61B 1/00087 600/104 |
| 8,246,575 B2 * | 8/2012 | Viola | A61B 1/00147 604/95.04 |
| 8,262,563 B2 | 9/2012 | Bakos et al. | |
| 8,571,711 B2 * | 10/2013 | Jacobsen | B08B 9/045 180/9.21 |
| 8,579,801 B2 * | 11/2013 | Konstorum | A61B 1/00071 600/128 |
| 8,608,648 B2 * | 12/2013 | Banik | A61B 1/00059 600/139 |
| 9,095,253 B2 * | 8/2015 | Hinman | A61B 1/0055 |
| 2006/0074407 A1 | 4/2006 | Padget et al. | |
| 2006/0178556 A1 | 8/2006 | Hasser et al. | |
| 2006/0199999 A1 | 9/2006 | Ikeda et al. | |
| 2009/0171147 A1 | 7/2009 | Lee et al. | |
| 2010/0094289 A1 | 4/2010 | Taylor et al. | |
| 2011/0028991 A1 | 2/2011 | Ikeda et al. | |
| 2013/0274741 A1 | 10/2013 | Marczyk et al. | |

FOREIGN PATENT DOCUMENTS

| | | |
|---|---|---|
| EP | 2140819 A1 | 1/2010 |
| WO | WO 97/17030 | 5/1997 |

\* cited by examiner

ELECTROSURGICAL DEVICE AND SYSTEM

RELATED APPLICATION(S)

This application is a Continuation Application of U.S. patent application Ser. No. 13/781,222, filed Feb. 28, 2013, which claims the benefit of priority under 35 U.S.C. 119(e) of U.S. Provisional Application No. 61/604,817 filed Feb. 29, 2012, all of which are incorporated herein by reference in its their entirety.

TECHNICAL FIELD

The present disclosure relates generally to medical devices and systems. In particular, to electrosurgical devices and manufacturing methods for producing the same.

BACKGROUND

During a medical procedure, an electrosurgical instrument may be used to cut, ablate, coagulate, or remove tissue. The electrosurgical instrument may comprise a distally located metal probe. The probe, or electrode, may be heated by an alternating electrical current operating in the radio frequency (RF) range. Alternatively, other types of electrodes or operating conditions may be used. The electrode may be operated at various conditions to ablate or coagulate tissue.

Many medical instruments include conductive components, such as metal cables or wires. Incorporating conductive parts into an electrosurgical instrument or an instrument that is paired with an electrosurgical instrument can increase the likelihood of a surgeon or patient getting shocked during the procedure. Electrical charge from the instrument's electrode may inadvertently arc to conductive parts of the instrument and travel to the surgeon's hands. In addition, saline, a fluid commonly used during surgery, can act as another conductive pathway. Unwanted electrical discharge may damage tissue of the patient located away from the surgical site. This damage may go undetected and complicate post-operative recovery.

Some current electrosurgical instruments are articulated to access sites within a patient's body that are difficult to reach using rigid non-articulating devices. For example, articulated RF ablation catheters provide steerable access to internal surfaces of the heart's chambers, often through tortuous vascular structures. Articulated medical devices have traditionally been flexible to provide easy manipulation. However, these devices often need various conductive or metal components to provide articulation. And as described above, conductive components provide pathways for unwanted electrical shocks.

The devices and systems for an electrosurgical instrument described herein overcome these and other limitations of the prior art. The devices and systems of the present disclosure are broadly applicable to various medical devices and other devices requiring articulation.

SUMMARY

In accordance with an embodiment, a medical instrument includes an articulation section operatively associated with an elongate articulation member configured to move the articulation section, wherein the articulation section can be configured to receive part of a conductive member. The instrument can also include an end effector having an electrode and a non-conductive section encasing a junction between the electrode and the conductive member, wherein the non-conductive section can be moveably coupled to the articulation section and can be fixedly coupled to the elongate articulation member.

In accordance with another embodiment, an end effector can include an electrically conductive section having an electrode and a conductive member electrically coupled to the electrode. The end effect can also include an electrically non-conductive section having a distal end, a proximal end, and at least partially encasing a portion of the electrically conductive section such that the electrode extends distally from the electrically non-conductive section and the conductive member extends proximally from the electrically non-conductive section, wherein the electrically non-conductive section can be configured to receive at least one elongate articulation member.

In accordance with yet another embodiment, a medical device can include an end effector having an electrode and a single-piece overmold. The overmold can include a lumen configured to receive the electrode and a conductive member, wherein the electrode and the conductive member are electrically coupled at a joint located within the lumen. The overmold can also include an anchoring mechanism configured to receive one or more articulation members. The medical device can further include an articulation section coupled to a proximal region of the overmold and operatively associated with the one or more articulation members. Also, the medical device can include a flexible elongate shaft coupled to a proximal region of the articulation section, wherein the shaft includes a proximal region coupled to a controller for controlling movement of the articulation section and a shield surrounding at least part of the conductive member that extends to the electrode.

In accordance with yet another embodiment, a method of forming a medical instrument can include forming an electrical connection between an electrode and a conductive member. The method can also include forming a polymer sheath over the electrical connection and forming an overmold over at least part of the polymer sheath, wherein the overmold can be coupled to an articulation joint. Next, the articulation joint may be located about at least part of the conductive member and an elongate control member extended through the articulation joint and anchored to the overmold. The method can also include coupling the articulation joint to the overmold.

Additional objects and advantages of the disclosure will be set forth in part in the description which follows, and in part will be obvious from the description, or may be learned by practice. The objects and advantages of the disclosure will be realized and attained by means of the elements and combinations particularly pointed out helm.

It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts. Also, any aspect set forth in any embodiment may be used with any other embodiment set forth herein.

Figure 1:
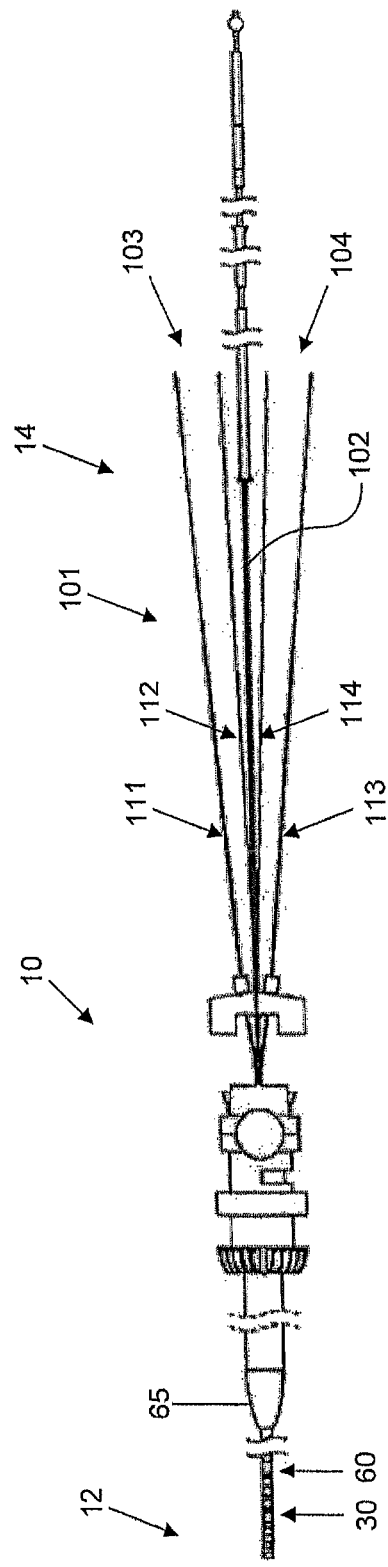
FIG. 1 is a side view of an instrument assembly, according to an exemplary embodiment.
Figure 2:
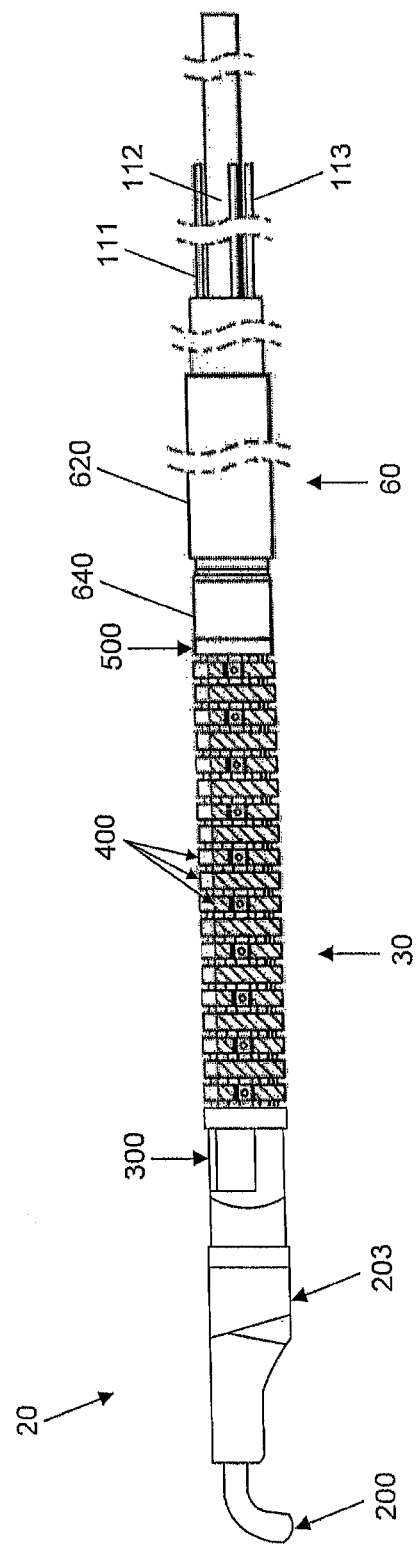
FIG. 2 is a side view of a distal end of the instrument assembly of FIG. 1.

FIGS. 1 and 2 show an instrument assembly 10 according to an exemplary embodiment. The instrument assembly 10 may be used for various therapeutic or diagnostic procedure and the steps thereof. In some embodiments, the instrument assembly 10 may be used with a medical procedure performed by inserting an endoscope, guide tube, catheter, or any other medical device into the body through any anatomic opening or incision. The instrument assembly 10 may then be passed through or used in conjunction with the inserted device.

The instrument assembly 10 may be used for performing surgery at a relative distance from a surgeon. The instrument assembly 10 may be adapted for, but not limited to, trans-oral, trans-anal, trans-vaginal, trans-urethral, trans-nasal, transluminal, endoscopic, laparoscopic, arthroscopic, thoracoscopic, orthopedic, through the ear, or percutaneous access. The components of the instrument assembly 10 described below may be made of any suitable material capable of being inserted into the body, e.g., a suitable biocompatible material.

The terms "proximal" and "distal" are used herein to refer to the relative positions of the components of the exemplary instrument assembly 10. When used herein, "proximal" refers to a position relatively closer to the surgeon using the instrument assembly 10. In contrast, "distal" refers to a position relatively further away from the surgeon using the instrument assembly 10 or closer to a surgical site located within the patient's body.

In addition, while the discussion of systems and methods below may generally refer to "surgical instruments," "surgery," or a "surgical site" for convenience, the described systems and their methods of use are not limited to tissue resection or repair. In particular, the described systems may be used for inspection and diagnosis in addition, or as an alternative, to surgical treatment. The treatment is not limited to any particular treatment. Various other exemplary treatment devices and methods are referred to herein.

The instrument assembly 10 may be configured to be advanced through any anatomical opening or body lumen. For example, the instrument assembly 10 may be used in natural orifice transluminal endoscopic surgery (NOTES) procedures or single incision laparoscopic surgical (SILS) procedures. Accordingly, the instrument assembly 10 may be shaped and sized for placement into a patient via a body cavity or an incision.

The instrument assembly 10 may have a distal end 12 and a proximal end 14. In order from the distal end 12 to the proximal end 14, the instrument assembly 10 may include an end effector 20, an articulation section 30, and an instrument shaft section 60. Part of instrument shaft may be flexible and part of instrument shaft may be rigid. For example, the instrument shaft section 60 may be flexible and an instrument shaft section 65 may be rigid.

The proximal end 14 of the instrument assembly 10 may include various mechanisms for allowing the user to control articulation or actuation of the distal end 12 of the instrument assembly 10. The proximal end 14 may include one or more knobs, handles, control members, or other devices configured to move the distal end 12 relative to the proximal end 14. Some exemplary components for controlling movement of the distal end of an instrument assembly are disclosed, for example, in U.S. Patent Application Publication No. 2008/0188868, entitled "Direct Drive Endoscopy Systems and Methods" and U.S. Provisional Application No. 61/593,209, filed Jan. 31, 2012, entitled "Medical Device Having Modular Handle," both of which are hereby incorporated by reference in their entirety.

Instrument assembly 10 may include a conductive member 102 configured to transmit an electrical signal. The electrical signal can include energy sufficient to ablate, coagulate, or cut tissue. The conductive member 102 may include a wire, a cable, a ribbon, or similar conductive component. In an exemplary embodiment, at least part of the conductive member 102 can include a coaxial cable. In place of or in addition to conductive member 102, instrument assembly 10 may include an actuation member (not shown). Instrument assembly 10 may be configured for monopolar or bipolar operation. Other portions of instrument assembly 10 may be configured for conduction, such as one or more articulation members 101.

One or more articulation members 101 may control the articulation of the articulation section 30 as described below. For example, the articulation members 101 may be braided wire. Articulation members 101 may be anchored distally along instrument assembly 10. For example, a distal end of the articulation member 101 may be fixedly attached to a distal part of articulation section 30.

In the exemplary embodiment shown in FIG. 1, the instrument assembly 10 may include two articulation members 103, 104. Each articulation member 103, 104 may extend from the proximal end 14 of the instrument assembly 10 to a articulation adapter 300 (described below) of the end effector 20, where the articulation member 103, 104 bends and extends back to the proximal end 14 of the instrument assembly 10. Thus, one articulation member 103 may include two articulation member portions 111 and 112 and a bend portion 116 (FIGS. 3A, 3B, and 5) connecting the portions 111 and 112. The other articulation member 104 may also include two articulation member portions 113 and 114 and another bend portion 117 (FIG. 3B) connecting the portions 113 and 114. The four articulation member portions 111, 112, 113, and 114 may control articulation of the articulation section 30 in four directions (e.g., right, up, left, and down, respectively). For example, when the operator pulls the first articulation member portion 111 or 113 in the proximal direction, the articulation section 30 may be articulated in the right or left direction, respectively. When the operator pulls the second articulation member portion 112 or 114 in the proximal direction, the articulation section 30 may be articulated in the up or down direction, respectively. Alternatively, the instrument assembly 10 may include only one articulation member portion, two articulation member portions, three articulation member portions, or more than four articulation member portions, depending on a desired range of movement of the instrument assembly 10.

Figure 3A:
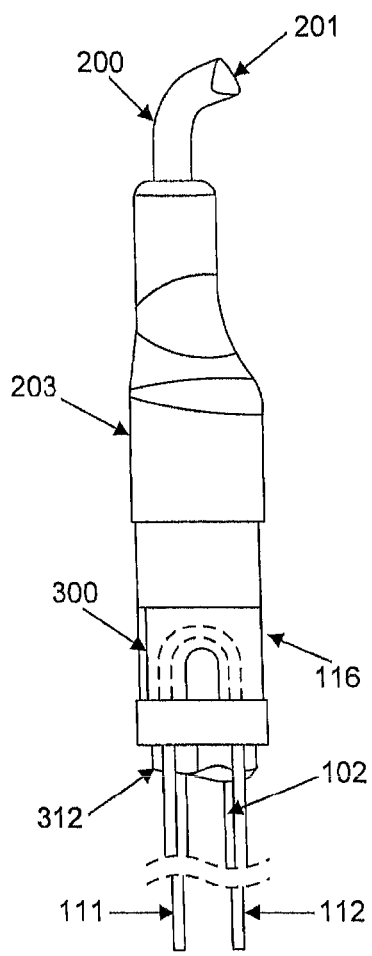
FIG. 3A is a perspective view of an end effector, according to an exemplary embodiment.
Figure 3B:
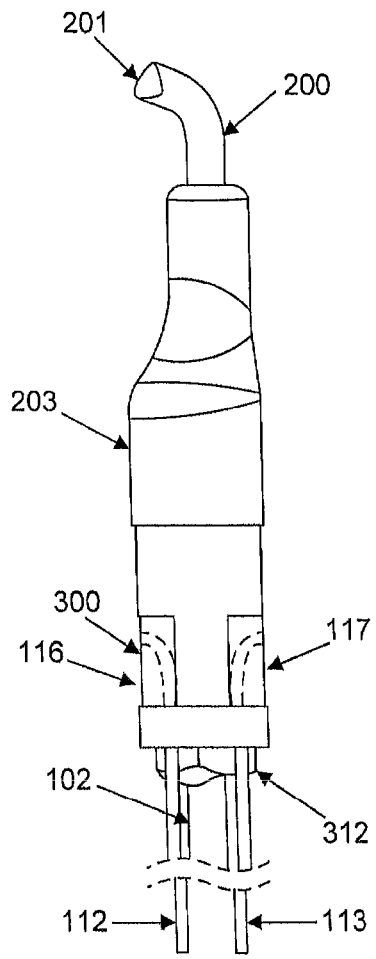
FIG. 3B is a perspective view of an end effector, according to an exemplary embodiment.
Figure 4:
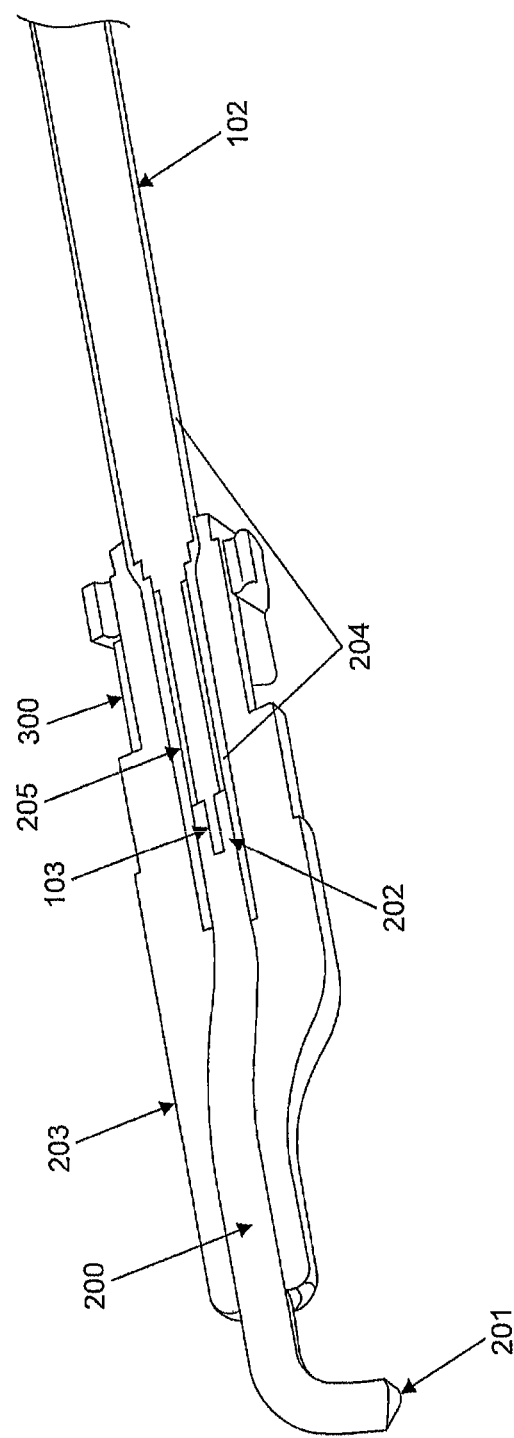
FIG. 4 is a cross-sectional view of an end effector, according to an exemplary embodiment.

FIGS. 3A, 3B, and 4 show the end effector 20 in the form of an electrosurgical instrument according to an exemplary embodiment. Alternatively, the end effector 20 may include a grasper, an ablation device, bipolar scissors, or other type of surgical or electrosurgical instrument configured to operate with, or include, insufflation, irrigation, suction, imaging, or other devices used in endoscopic, laparoscopic, or other surgical procedures. In addition, the end effector 20 may be a needle-electrode configured to allow fluid flow in or out.

The distal end of the end effector 20 of the exemplary embodiment may include a hook portion 200. The hook portion 200 may include an electrode 201 formed of a conductive material, wherein the electrode 201 is configured to contact and provide energy to tissue. For example, the hook portion 200 may be formed of a conductive metal. A distal end of the hook portion 200 may have a substantially triangular cross-sectional shape. In addition, triangular cross-sectional shape may include two substantially rounded corners and one substantially pointed corner. Alternatively, the hook portion 200 may be circular, oval, rectangular, or any appropriate cross-sectional shape to provide any desired therapeutic effect. Furthermore, the cross-sectional geometry may change across the length of the hook portion 200, as appropriate.

The hook portion 200 may be connected to conductive member 102. For example, a distal end 103 of the conductive member 102 may extend into a proximal end 202 of the hook portion 200. The distal end 103 of the conductive member 102 may include a wire configured to provide an ablative current and voltage to electrode 201.

In some embodiments, the distal end 103 of the conductive member 102 may be soldered to the proximal end 202 of the hook portion 200. Alternatively, the distal end 103 of the conductive member 102 may be connected to the proximal end 202 of the hook portion 200 by other means known in the art. For example, the distal end 103 of the conductive member 102 may be connected to the proximal end 202 of the hook portion 200 by, for example, crimping, welding, swaging, threading, or brazing.

The distal end 103 of the conductive member 102 and the proximal end 202 of the hook portion 200 may be encased in a polymer layer 204, as shown in FIG. 4. The polymer layer 204 may be a polyimide thermoset polymer or other suitable polymer capable of maintaining a mechanical stability at high temperature. For example, a polyimide bushing may surround the junction between the hook portion 200 and the conductive member 102.

The polymer layer 204 may provide mechanical and electrical benefits. For example, the polymer layer 204 may protect and enforce the joint between the distal end 103 of the conductive member 102 and the proximal end 202 of the hook portion 200. This may help reduce "whipping" of the hook portion 200, by acting as a damper to absorb some of the forces generated during use of instrument assembly 10. The polymer layer 204 may also help prevent loss of connection between the distal end 103 of the conductive member 102 and the proximal end 202 of the hook portion 200.

The end effector 20 may further include a polymer layer 205. Polymer layer 205 may be located between the polymer layer 204 and at least part of the hook portion 200 or the conductive member 102. The polymer layer 205 may fill a gap located beneath the polymer layer 204 and may include an epoxy or other material.

The end effector 20 of the exemplary embodiment may also include an overmold portion 203. The overmold portion 203 may be formed of a non-conductive material. For example, the overmold portion 203 may be formed of a non-conductive polymer such as grivory or a glass filled nylon type material. In other embodiments, the end effector 20 may lack one or more polymer layers 204, 205. In such an embodiment, the overmold portion 203 may directly contact part of the hook portion 200 or the conductive member 102. Any portion of the surfaces of hook portion 200 or conductive member 102 may have surface modifications (e.g., roughening, divots, or bumps) to improve the attachment of the overmold portion 203 to the device.

The overmold portion 203 may encase the proximal end 202 of the hook portion 200 and the distal end 103 of the conductive member 102. In addition, the overmold portion 203 may encase at least a portion of the polymer layer 204. For example, the overmold portion 203 may include a lumen extending therethrough configured to receive the proximal end 202 of the hook portion 200 and the distal end 103 of the conductive member 102. The lumen may also be configured to receive the portion of the polymer layer 204.

The conductive member 102 and the polymer layer 204 may taper near proximal end of the overmold portion 203. The taper may allow for additional overmold material to encase the proximal end 202 of the hook portion 200 and the distal end 103 of the conductive member 102. In addition, at least a portion of an outer surface of the overmold portion 203 may include a taper. The taper may narrow toward a distal end of the overmold portion 203.

The proximal end of the overmold portion 203 may include an articulation adapter 300 configured to couple to a distal end of the articulation section 30. The articulation section 30 may also include a series of articulation links 400 and a proximal adapter 500 for connecting to the instrument shaft section 60. Some exemplary configurations of articulation links and articulation sections are disclosed, for example, in U.S. patent application Ser. No. 13/360,018, filed Jan. 27, 2012, entitled "Articulation Joints for Torque Transmission," which is hereby incorporated by reference in its entirety.

In other embodiments, the overmold portion 203 may be coupled to various articulation joints. For example, the articulation section 30 could be formed using a elastic material configured to flex to provide articulation. It is also contemplated that various components of the end effector 20 and the articulation section 30 could be formed into one or more parts. For example, the overmold portion 203 and at least part of the articulation section 30 could be formed into a single molded piece. Such a single component combing the functions of the overmold portion 203 and the articulation section 30 could be coupled to the instrument shaft section 60.

By integrating the articulation adapter 300 into the overmold portion 203, a metal component may be eliminated from the instrument. Other parts and an interface can also be eliminated. This design may provide a more efficient coupling between the end effector 20 and the articulation section 30. This design also may reduce electrical arcing and subsequently the chance of the surgeon getting shocked and the patient receiving unnecessary tissue damage. For example, the articulation adapter 300 may isolate part of the articulation members 101 from stray electrical charge. In addition, the articulation adapter 300 may seal the articulation section 30, substantially preventing the influx of fluid into the articulation section 30. Without this function, coagulation of blood on the conductive member 102, the articulation members 101 or articulation links 400 may reduce the ability of the instrument assembly 10 to properly articulate and actuate.

In addition, fluid buildup within the articulation section 30 may increase pressure within the articulation section 30 and cause bond failures between components forming the articulation section 30. These bond failures may compromise the electrical insulation properties of the instrument assembly 10 and may also allow additional debris to enter the articulation section 30 and further reduce the ability of the instrument assembly 10 to articulate and actuate. This fluid may also increase the thermal runaway and the electrical conductivity of the instrument assembly 10, increasing the surgeon's chance of getting shocked by the electricity and the chance of creating electrical discharge outside the surgeon's view.

Figure 6:
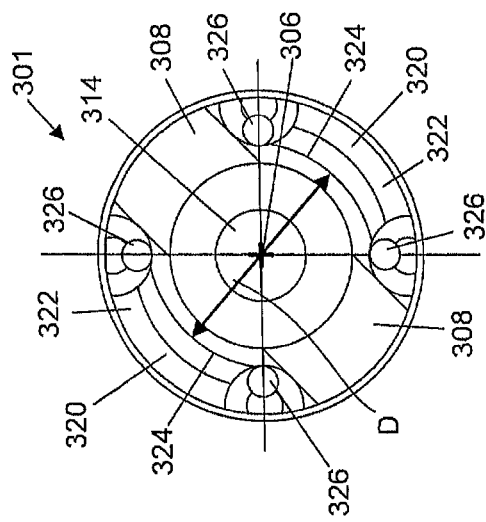
FIG. 6 is a cross-sectional view of the body of the articulation adapter of FIG. 5.
Figure 5:
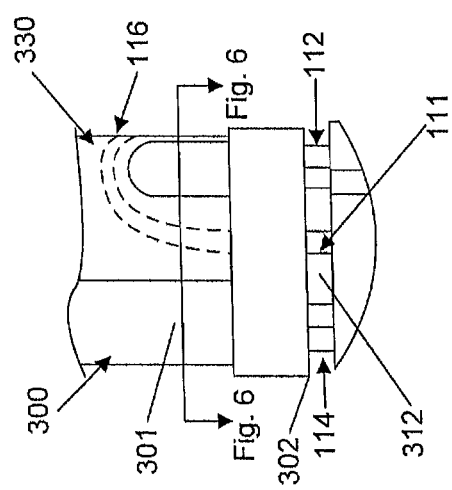
FIG. 5 is a side view of a proximal end of an end effector showing a part of an end effector body including an articulation adapter, according to an exemplary embodiment.

FIGS. 5 and 6 show the proximal end of the overmold portion 203 of the end effector 20 including the articulation adapter 300, according to an exemplary embodiment. The articulation adapter 300 may include a body 301 and one or more anchoring members 330 that may fix the bend portions 116 of the articulation members to the body 301. Each of the articulation members 101 may extend in the proximal direction from the articulation adapter 300. The body 301 includes a proximal end 302.

The proximal end 302 of the body 301 may include a proximal protrusion 312 configured to be coupled or attached to the distalmost articulation link 400 of the series of articulation links 400. In the exemplary embodiment, the proximal protrusion 312 may be rectangular and may be received within a corresponding rectangular cavity in the distalmost articulation link 400. The proximal protrusion 312 may also include a curved proximal surface (e.g., concave or curved outward toward the proximal direction) to allow the articulation adapter 300 to engage a corresponding curved surface (e.g., convex or curved inward) of the distalmost articulation link 400, as shown in FIGS. 3A and 3B. The connection between the proximal protrusion 312 and the distalmost articulation link 400 may be configured to permit movement between the overmold portion 203 and the articulation section 30.

As shown in FIG. 6, the body 301 of the articulation adapter 300 may also include one or more cable member channels 314. In the exemplary embodiment, the body 301 includes one cable member channel 314 that has an axis that is substantially collinear with a longitudinal axis 306 of the body 301. The cable member channel 314 may slidably receive the conductive member 102 (FIGS. 1, 3A, 3B, and 7A) to allow the conductive member 102 to pass through the articulation adapter 300.

The body 301 of the articulation adapter 300 may also include one or more cavities 320 for supporting the one or more articulation members received by the body 301. In the exemplary embodiment, the body 301 includes two side cavities 320 positioned at opposite sides of the body 301 relative to the longitudinal axis 306. Each side cavity 320 may be partially defined by a respective pedestal or ledge 322 and an inner surface 324. The inner surface 324 may extend generally along the direction of the longitudinal axis 306 and may have a diameter D (FIG. 6) measured along a plane perpendicular to the longitudinal axis 306. As shown in FIG. 6, the diameter D may be smaller than an outer diameter of the body 301. The ledges 322 may form a curved surface such that an outer surface of the curve faces the distal direction (e.g., concave or curved outward toward the distal direction).

In the exemplary embodiment shown in FIGS. 5 and 6, the ledges 322 and inner surfaces 324 may support the respective articulation member (e.g., the bend portions 116) received in the body 301. Alternatively, the bend portions 116 may be supported by the inner surfaces 324 and may extend distal to the ledges 322.

The articulation adapter 300 may support the bend portions 116 of the articulation members so that the articulation members do not form a kink. In the exemplary embodiment shown in FIGS. 5 and 6, to reduce the likelihood of forming kinks, the ledges 322 may be formed as elliptical arcs (portions of ellipses), and the dimensions of the elliptical arcs may depend on a dimension of the articulation adapter 300 (e.g., the diameter D (FIG. 6)) or a configuration of the articulation member (e.g., the size of the braid). Alternatively, the ledges 322 may form another type of curved bend instead of an elliptical arc, such as a semicircular bend, the dimensions of which may also depend on a dimension of the articulation adapter 300 or a configuration of the articulation member.

Referring to FIG. 6, each side cavity 320 may connect to one or more articulation member channels 326. The articulation member channels 326 may extend from the side cavities 320 to the outer surface of the body 301 from which the proximal protrusion 312 extends. In the exemplary embodiment shown in FIG. 6, the body 301 includes four articulation member channels 326 positioned at approximately 0, 90, 180, and 360 degrees, respectively, about the cable member channel 320 relative to the longitudinal axis 306. The articulation member channels 326 may slidably receive the respective articulation members 101 that are proximal to the bend portions 116 to allow the articulation members 101 to extend in the proximal direction from the articulation adapter 300.

FIG. 5 shows the anchoring members 330 disposed within the side cavities 320, respectively. The anchoring members 330 may be formed in the side cavities 320 after the articulation members (e.g., the bend portions 116) are positioned on the respective ledges 322 or the inner surfaces 324. The anchoring members 330 may be attached to the body 301 by adhesion or cohesion, e.g., using an adhesive or a polymer. The anchoring members 330 may also be molded in.

In an exemplary embodiment, the anchoring members 330 may be formed by epoxy (e.g., a one- or two-part epoxy) or other thermosetting polymer that may be inserted into and at least partially fill the side cavities 320 to fix the bend portions 116 to the ledges 322 or the inner surfaces 324. Alternatively, the anchoring members 330 may be formed by polyether ether ketone (PEEK), solder, or other material capable of melting at a temperature that is lower than the melting point of the material forming the body 301. In an exemplary embodiment, the anchoring members 330 may be formed so that an outer surface of the anchoring members 330 and an outer surface of the body 301 form a generally cylindrical outer surface, as shown in FIG. 5. The anchoring members 330 may substantially cover the bend portions 116 and fix the bend portions 116 to the respective ledges 322 or inner surfaces 324.

Figure 7A:
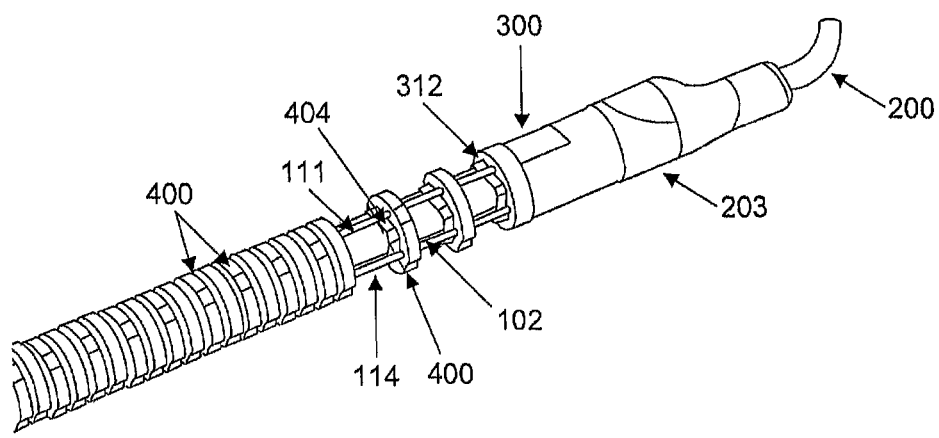
FIG. 7A is an exploded perspective view of an articulation section, according to an exemplary embodiment.

After fixing the articulation members to the articulation adapter 300, the articulation members 101 may be inserted through corresponding channels in the plurality of articulation links 400 to allow the articulation members 101 to pass through the articulation links 400. FIG. 7A shows the insertion of the articulation members 101 through the plurality of articulation links 400 prior to positioning the articulation links 400 together as shown in FIG. 2.

Figure 7B:
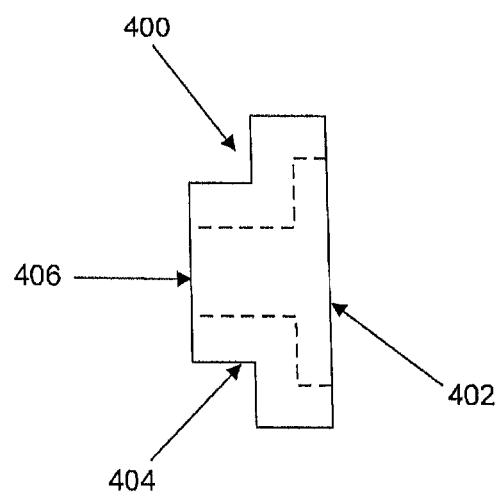
FIG. 7B is a side view of an articulation link of the articulation section of FIG. 7A.

As shown in FIGS. 7A and 7B, each articulation link 400 may include a substantially cylindrical outer surface, and may include a cavity 402 on its distal end and a protrusion 404 on its proximal end. Each articulation link 400 may also be coated with an insulative material. The protrusions 404 of each articulation link 400 may have a similar shape as the proximal protrusion 312 of the articulation adapter 300. When the articulation members connect the articulation adapter 300 to the articulation links 400, the proximal protrusion 312 of the articulation adapter 300 may be inserted into the cavity 402 in the distalmost (first) articulation link 400, the protrusion 404 on the first articulation link 400 may be inserted into the cavity 402 in the second articulation link 400, the protrusion 404 on the second articulation link 400 may be inserted into the cavity 402 in the third articulation link 400, etc.

In an exemplary embodiment, the protrusions 404 of the articulation links 400 may be generally rectangular. The cavities 402 in the articulation links 400 may be defined by one or more inner surfaces, and may be generally rectangular in order to receive the corresponding protrusions 312, 404. Alternatively, the cavities 402 and protrusions 312, 404 may have another shape. The articulation adapter 300, the articulation links 400, and the proximal adapter 500 allow the articulation section 30 to articulate as described above.

Each articulation link 400 may also include an inner surface defining one or more cable member channels 406. In the exemplary embodiment, each articulation link 400 includes one cable member channel 406 having an axis substantially collinear with a longitudinal axis of the articulation link 400 and extending through the articulation link 400. The cable member channel 406 may slidably receive the conductive member 102 (FIGS. 1, 3A, 3B, 7A, and 7B) to allow the conductive member 102 to extend between the end effector 20 and the proximal end 14 of the instrument assembly 10.

Figure 8:
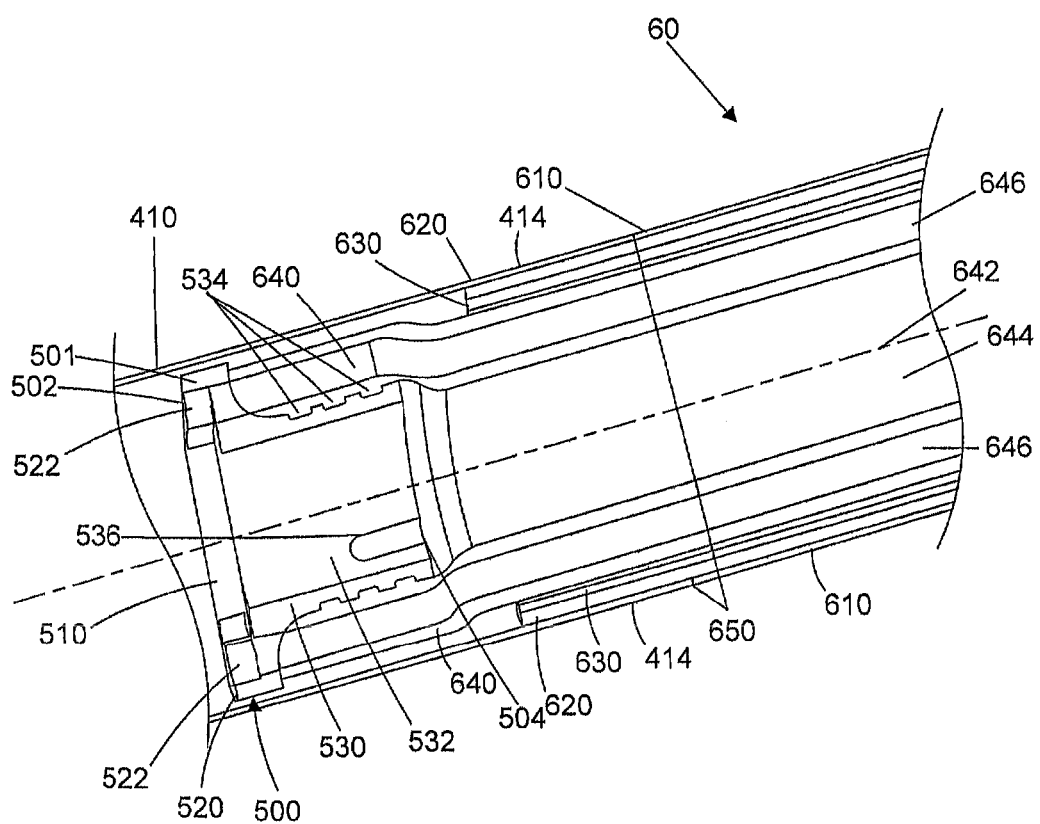
FIG. 8 is a cross-sectional perspective view of the sheath of the articulation section and the instrument shaft section.
Figure 9:
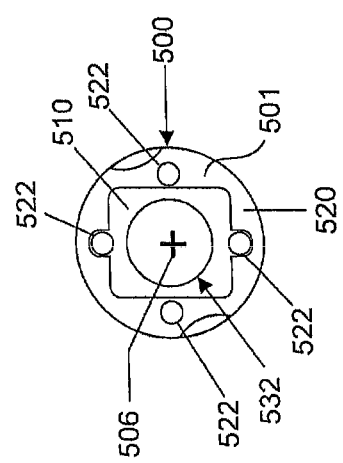
FIG. 9 is a front view of the proximal adapter of FIG. 8.

FIGS. 8 and 9 show the proximal adapter 500 of the articulation section 30. The proximal adapter 500 may connect to the distal end of the instrument shaft section 60. Some exemplary configurations of instrument shafts are disclosed, for example, in U.S. Provisional Application No. 61/593,121, filed Jan. 31, 2012, entitled "Method and System For Attaching An Articulation Section to A Medical Device," which is hereby incorporated by reference in its entirety. The proximal adapter 500 may include a body 501 including a distal end 502, a proximal end 504, and a longitudinal axis 506 extending between the distal and proximal ends 502 and 504. In the exemplary embodiment, the body 501 may be formed of a rigid material, such as stainless steel or a polymer, such as a polyimide. Alternatively, at least part of the body 501 may be formed of PEEK, a high modulus polymer, or a high temperature resistant polymer. Also, in an exemplary embodiment, the length or longitudinal dimension of the body 501 may be less than or equal to approximately 0.12 inches.

The distal end 502 of the body 501 may include a distal cavity 510 sized to receive the protrusion 404 on the proximalmost articulation link 400. In the exemplary embodiment shown in FIGS. 8 and 9, the distal cavity 510 may be defined by one or more inner surfaces, and may have the same shape (e.g., rectangular) as the protrusion 404 on the proximalmost articulation link 400 in order to receive the protrusion 404.

The distal end 502 of the body 501 may also include a flange 520. The flange 520 may be generally cylindrical and may include a plurality of articulation member channels 522 extending between the distal and proximal surfaces of the flange 520. In the exemplary embodiment, the flange 520 may include four articulation member channels 522 that may be spaced from each other. For example, the four articulation member channels 522 may be positioned at approximately 0, 90, 180, and 360 degrees, respectively, about the distal cavity 510 relative to the longitudinal axis 506, or at other angles. The articulation member channels 522 may slidably receive the respective articulation members 101 to allow the articulation members 101 to pass through the proximal adapter 500.

The proximal end 504 of the body 501 may include a tubular portion 530 that extends from the flange 520 in the proximal direction. The tubular portion 530 may have a substantially cylindrical outer surface and may include an inner surface defining one or more cable member channels 532. In the exemplary embodiment shown in FIGS. 8 and 9, the body 301 may include one cable member channel 532 having an axis substantially collinear with the longitudinal axis 506 of the body 501. The cable member channel 532 may be substantially cylindrical and may connect to the distal cavity 510, which also has an axis that may be collinear with the longitudinal axis 506 of the body 501 and may have a different width or lateral dimension (e.g., diameter) than the cable member channel 532. For example, as shown in FIGS. 8 and 9, the cable member channel 532 may have a diameter that is smaller than the dimensions of the distal cavity 510.

The distal cavity 510 and the cable member channel 532 may slidably receive the conductive member 102 (FIGS. 1, 8, and 9) to allow the conductive member 102 to extend between the end effector 20 and the proximal end 14 of the instrument assembly 10. In an exemplary embodiment, the length or longitudinal dimension of the tubular portion 530 (e.g., the distance between the proximal surface of the flange 520 to the proximal surface of the tubular portion 530) may be less than or equal to approximately 0.10 inches. As shown in FIG. 8, the tubular portion 530 of the proximal adapter 500 may be inserted into the instrument shaft section 60.

In an exemplary embodiment, the instrument shaft section 60 may include an outer first layer 610 (FIG. 8), a second layer 620, a third layer 630, and a catheter or inner tubular portion 640 forming a fourth layer. The inner tubular portion 640 may be formed of a flexible material, such as a polymer, polyimide, etc. In an exemplary embodiment, the inner tubular portion 640 may be formed of nylon (e.g., nylon 12, Rilsan® AESNO) extruded to form the inner tubular portion 640.

As shown in FIG. 8, the inner tubular portion 640 may have a generally cylindrical outer surface and may have a longitudinal axis 642. The inner tubular portion 640 may also include a plurality of lumens or channels. For example, the inner tubular portion 640 may include one or more cable member channels 644, and one or more articulation member channels 646. The inner tubular portion 640 includes one cable member channel 644 having an axis substantially collinear with the longitudinal axis 642. The cable member channel 644 may be generally cylindrical and may slidably receive the conductive member 102 (FIGS. 1, 8, and 9). The tubular portion 530 of the proximal adapter 500 may be inserted into the cable member channel 644 of the inner tubular portion 640 so that the cable member channel 644 may align with the cable member channels 314, 406, and 532 in the articulation adapter 300, the articulation links 400, and the proximal adapter 500. As a result, the conductive member 102 may pass through the cable member channels 314, 406, 532, and 644 to extend between the end effector 20 and the proximal end 14 of the instrument assembly 10.

Also, the inner tubular portion 640 may include four articulation member channels 646 that may be spaced from each other. For example, the four articulation member channels 646 may be positioned at approximately 0, 90, 180, and 360 degrees, respectively, about the cable member channel 644 relative to the longitudinal axis 642, or at other angles. The articulation member channels 646 may slidably receive the respective articulation members 101. When the tubular portion 530 of the proximal adapter 500 is inserted into the inner tubular portion 640, the articulation member channels 646 may align with the articulation member channels 326 and 522 in the articulation adapter 300, the articulation links 400, and the proximal adapter 500 to allow the articulation members 101 to extend between the articulation adapter 300 and the proximal end 14 of the instrument assembly 10.

The tubular portion 530 of the proximal adapter 500 may be inserted into the inner tubular portion 640 until a proximal surface of the flange 520 of the proximal adapter 500 abuts the distal end of the inner tubular portion 640.

The outer dimension (e.g., outer diameter) of the tubular portion 530 of the proximal adapter 500 may be larger than the dimension (e.g., diameter) of the cable member channel 644 of the inner tubular portion 640 before the tubular portion 530 is inserted into the inner tubular portion 640. Thus, although the inner tubular portion 640 may be formed with a substantially constant outer diameter and inner diameter, the insertion of the tubular portion 530 of the proximal adapter 500 may cause the inner tubular portion 640 to expand radially, as shown in FIG. 8. As a result, the inner tubular portion 640 may provide a radial pressure or force on the tubular portion 530 of the proximal adapter 500 such that the tubular portion 530 may be held in place in the inner tubular portion 640 (e.g., to assist in preventing the tubular portion 530 from inadvertently slipping out of the inner tubular portion 640).

The outer surface of the tubular portion 530 of the proximal adapter 500 may include one or more circumferential ribs 534. In the exemplary embodiment shown in FIG. 8, the tubular portion 530 includes three ribs 534, and the ribs 534 extend around substantially the entire circumference of the tubular portion 530. Alternatively, the ribs 534 may extend around a portion of the circumference. The ribs 534 may assist in maintaining the tubular portion 530 anchored in the inner tubular portion 640 of the instrument shaft section 60, e.g., by providing resistance to movement of the tubular portion 530 in the longitudinal direction.

The tubular portion 530 of the proximal adapter 500 may also include one or more notches 536. In the exemplary embodiment shown in FIG. 8, the tubular portion 530 includes one notch 536 extending generally parallel to the longitudinal axis 506 (FIG. 9). The notch 536 may extend along the radial direction through the tubular portion 530. The notch 536 may also extend along the longitudinal direction from the proximal end 504 of the body 501 past at least one of the ribs 534 (e.g., one, at least two, or all of the ribs 534). The notch 536 may assist in maintaining the tubular portion 530 anchored in the inner tubular portion 640 of the instrument shaft section 60, e.g., by providing resistance to torsional movement of the tubular portion 530.

As shown in FIG. 8, the articulation section 30 may also include a cover or sheath 410 that covers at least a portion of the articulation section 30. The sheath 410 may also cover at least a portion of the end effector 20. For example, the sheath 410 may cover articulation adapter 300. The sheath 410 may be formed of one or more polymers, such as thermoplastic polyurethane (e.g., Pellethane®) or other polyurethane plastic or elastomer, or other thermoplastic elastomer, or other flexible polymer. The sheath 410 may be formed of a material, such as a layer of Pellethane®, that is relatively difficult to tear and is flexible.

The sheath 410 may act as a barrier between the patient and the components of the articulation section 30. For example, the sheath 410 may limit occlusion formation in extracellular fluid of the patient within the articulation section 30. Occlusions in the articulation section 30 may reduce the ability to articulate or actuate the instrument assembly 10.

The material used for forming the sheath 410 may be flexible. As the instrument assembly 10 articulates, the sheath 410 may be able to stretch and maintain a higher durometer (hardness) to prevent breakage of the sheath 410. As a result, the sheath 410 may be thinner, which may allow the operator to more easily insert the instrument assembly 10 in the patient.

Also, the sheath 410 may serve as a barrier that electrically insulates electrically conductive components in the articulation section 30 from other components that may carry an electric current, such as a metal tip of an electrosurgical instrument used in conjunction with the instrument assembly 10. As a result, the sheath 410 may prevent possible burning of the patient or shocks to the surgeon due to the inadvertent conduction of electrical current through the instrument assembly 10.

As described below in connection with FIG. 8, at least a portion of the sheath 410 may overlap and bond to at least a portion of the instrument shaft section 60, e.g., so that the sheath 410 and the first layer 610 of the instrument shaft section 60 can provide a continuous flexible or insulative barrier.

FIG. 8 shows an exemplary embodiment in which the sheath 410 of the articulation section 30 may be attached to the instrument shaft section 60. The sheath 410 may include at least a portion 414 that overlaps and may be attached (e.g., using an adhesive) to a component of the instrument shaft section 60 that may be formed of a material that is not lubricious (e.g., a non-fluorinated material), as described below. As a result, the sheath 410 may be attached to the instrument shaft section 60 to form with the outer first layer 610 a continuous and flexible barrier to fluids and electrical current.

The instrument assembly 10 may be formed using various manufacturing methods. In one embodiment, the distal end 103 of the conductive member 102 may be stripped to expose interior portions of the conductive member. An exposed braid may require treatment to prevent parts of the braid protruding or otherwise increasing the likelihood of shorting. The exposed braid may be rotary cut.

During manufacturing, the polymer layer 204 may be slid over the conductive member 102 prior to the distal end 103 of the conductive member 102 and the proximal end 202 of the hook portion 200 being connected. Subsequently, the electrode 201 may be electrically coupled to the conductive member 102. For example, an electrical connection can be formed between the electrode 201 and the conductive member 102 using various techniques, such as, soldering, welding, crimping, friction fit, riveting, using a screw, a pin, an adhesive, or other mechanism.

Following formation of electrical connection, the polymer layer 204 may be located about the electrical connection. As shown in FIG. 4, the polymer layer 204 may surround a proximal region of the hook portion 200 and a distal region of conductive member 102. Heat shrinking, thermosetting, and other techniques may be used to form the polymer layer 204 about at least part of the electrical connection.

Injection of the polymer layer 205 may occur at various times during the manufacturing process. For example, the polymer layer 205 may be applied through a hole created in the polymer layer 204. A gap between the polymer layer 204 and at least part of the conductive member 102 or the hook portion 200 may be at least partially filled by the polymer layer 205 or another suitable material. As described above, end effector 20 can be formed without one or more polymer layers 204, 205.

Overmold portion 203 may then be formed over at least part of the polymer layer 204. In some embodiments, a material used to form the overmold portion 203 may be non-conductive. Thermoplastics, polymers, injectable materials, or other similar materials may be used. The overmold portion 23 may also include internal reinforcing, such as, for example, glass fibers. Injection molding, thermosetting, layering, or other techniques could be used to form the overmold portion 203. The overmold may be formed by potting or low-pressure casting. A fill time and a gate location may be selected based on a maximum shear rate, a packing profile, a cooling time, an overmold material, a ram profile, a clamp force, or a vent location. In some embodiments, a grivory 3H material may be used to form at least part of the overmold portion 203.

As described above, articulation section 30 may be coupled to the overmold portion 203. In some embodiments, the overmold portion 203 may be moveably coupled to the articulation section. As described above, the proximal protrusion 312 of the overmold portion 203 may include a surface configured to movingly couple to a corresponding surface located on a distal region of articulation section 30. Other couplings between the overmold portion 203 and articulation section 30 are also possible. For example, a ball and socket, a pivot, or a flexible material coupling could be used.

One or more conductive members 102 or articulation members 101 may be extended through the articulation section 30. As described above, one or more articulation members 101 may be anchored to the overmold portion 203. Anchoring may use an adhesive, a friction fit, a crimp or other mechanism to fixedly attached part of the articulation members 101 relative to the overmold portion 203.

A proximal region of the articulation section 30 may be coupled to the instrument shaft section 60. As described above, the instrument shaft section 60 can be flexible, include one or more channels configured to receive various elongate members, and may be formed of various polymers.

Various parts of instrument assembly 10 can include electrical shielding. Shielding can include conductive components configured to transfer unwanted electrical energy away from certain parts of instrument assembly 10. For example, conductive component 102 can include a protective co-axial shield located about a primary conductive cable. In some embodiments, the protective co-axial shield may terminate proximal to the hook portion 200, the overmold portion 203, or the articulation section 30. The shield may also be electrically connected to one or more conductive components, such as, for example, part of articulation section 30, the articulation members 101, or the proximal adapter 500.

It will be apparent to those skilled in the art that various modifications and variations can be made in the disclosed systems and processes without departing from the scope of the disclosure. Other embodiments of the disclosure will be apparent to those skilled in the art from consideration of the specification and practice of the disclosure disclosed herein. It is intended that the specification and examples be considered as exemplary only.

What is claimed is:

1. A medical device, comprising:
   a first section including an elongate member, wherein the elongate member is configured to articulate;
   a second section including an electrically conductive section, wherein the electrically conductive section is configured to move relative to the elongate member; and
   at least one connecting member partially disposed within the first section and partially disposed within the second section, wherein the at least one connecting member is configured to move the elongate member.

2. The medical device of claim 1, wherein at least a portion of the first section is configured to receive at least a portion of the second section.

3. The medical device of claim 1, wherein a proximal end of the second section is moveably coupled to the distal end of the first section.

4. The medical device of claim 1, further comprising an anchoring mechanism configured to fixedly attach the at least one connecting member to the second section.

5. The medical device of claim 4, wherein the anchoring mechanism is a portion of the second section configured to receive a bend portion of the at least one connecting member.

6. The medical device of claim 1, wherein the second section includes an electrode.

7. A medical device, comprising:
   a shaft section;
   an elongate member at least partially distal to the shaft section and configured to articulate relative to the shaft section; and
   an end effector including an electrically conductive section and a non-conductive section, wherein the end effector is moveably coupled to the elongate member, wherein a proximal end of the end effector is curved.

8. The medical device of claim 7, further comprising articulation members configured to articulate the elongate member.

9. The medical device of claim 8, further comprising an anchoring mechanism configured to fixedly attach at least one of the articulating members to the end effector.

10. The medical device of claim 9, wherein the anchoring mechanism is a portion of the end effector configured to receive a bend portion of the at least one of the articulation members.

11. The medical device of claim 7, wherein a proximal end of the end effector includes a proximal protrusion configured to be moveably coupled to a distalmost end of the elongate member.

12. The medical device of claim 7, further comprising a sheath, wherein the sheath covers a least a portion of the elongate member and a portion of the end effector.

13. The medical device of claim 7, wherein the end effector includes an electrode.

14. A medical device comprising:

an end effector including a single-piece overmold;

an anchoring mechanism configured to receive one or more articulation members that extend to a proximal end of the medical device, wherein the anchoring mechanism is a portion of the end effector configured to receive a bend portion of the one or more articulation members and is configured to fixedly attach the one or more articulation members to the end effector;

an articulation section moveably coupled to a proximal region of the overmold; and a flexible elongate shaft coupled to a proximal region of the articulation section, wherein the articulation section is configured to articulate relative to the flexible elongate shaft.

15. The medical device of claim 14, wherein the articulation section is operatively associated with the one or more articulation members.

16. The medical device of claim 14, wherein the end effector includes an electrode.

17. The medical device of claim 14, wherein the overmold is formed of a non-conductive material.

18. The medical device of claim 14, wherein the overmold encases a distal end of a conductive section.

* * * * *